US009625424B2

(12) United States Patent
LePage et al.

(10) Patent No.: US 9,625,424 B2
(45) Date of Patent: Apr. 18, 2017

(54) SYSTEM AND A METHOD OF AUTOMATICALLY GENERATING A PHASED ARRAY ULTRASOUND SCAN PLAN FOR NON-DESTRUCTIVE INSPECTION

(71) Applicants: Benoit LePage, Québec (CA); Martin St-Laurent, Québec (CA)

(72) Inventors: Benoit LePage, Québec (CA); Martin St-Laurent, Québec (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 274 days.

(21) Appl. No.: 14/621,906

(22) Filed: Feb. 13, 2015

(65) Prior Publication Data
US 2016/0238566 A1  Aug. 18, 2016

(51) Int. Cl.
*G01N 29/04* (2006.01)
*G01N 29/26* (2006.01)

(52) U.S. Cl.
CPC ........... *G01N 29/262* (2013.01); *G01N 29/04* (2013.01); *G01N 2291/023* (2013.01); *G01N 2291/0289* (2013.01); *G01N 2291/267* (2013.01)

(58) Field of Classification Search
CPC ................. G01N 29/262; G01N 29/04; G01N 2291/267; G01N 2291/0289
See application file for complete search history.

(56) References Cited

U.S. PATENT DOCUMENTS

| | | | | |
|---|---|---|---|---|
| 6,405,596 B1* | 6/2002 | Kruzic | ................... | G01N 29/11 73/1.82 |
| 6,789,427 B2* | 9/2004 | Batzinger | ............ | G01N 29/069 73/614 |
| 7,966,860 B2* | 6/2011 | Dijkstra | ............... | G01N 29/225 73/1.82 |
| 8,783,111 B2* | 7/2014 | Matsumoto | .......... | G01N 29/043 73/599 |
| 9,032,802 B2* | 5/2015 | Imbert | .................... | G01N 29/27 73/622 |
| 9,207,214 B2* | 12/2015 | S | ............................ | G01N 29/04 |
| 9,250,212 B2* | 2/2016 | S. | .......................... | G01N 29/262 |
| 9,372,173 B2* | 6/2016 | Thomson | ............. | G01N 29/221 |
| 2007/0000328 A1* | 1/2007 | Buttram | ................... | G01H 5/00 73/597 |
| 2007/0068253 A1* | 3/2007 | Carodiskey | ........ | G01N 29/0618 73/570 |

(Continued)

*Primary Examiner* — Harshad R Patel
*Assistant Examiner* — Samir M Shah (57) ABSTRACT

Disclosed is phased array inspection system with automatically generated PAUT scan plan based on a set of configurable probe operation parameters and a combination of preferred code requirement and rules given by PAUT expertise. The complex code requirements and PAUT expertise are pre-assembled into a plurality of templates applicable to categories of inspection tasks by PAUT experts. Requirements and optimization scoring schemes are then used to automatically score each of specifically proposed scan plan setup, including the selection of probe operation parameters against the corresponding template for a specific task. This allows less skilled field inspector to operate with the correct interpretation of the complex code and accurate evaluation of the scan plan.

25 Claims, 7 Drawing Sheets

(56) References Cited

U.S. PATENT DOCUMENTS

| | | | |
|---|---|---|---|
| 2009/0199642 A1* | 8/2009 | Fukutomi | G01N 29/069 73/598 |
| 2009/0320601 A1* | 12/2009 | Kleinert | G01N 29/0618 73/628 |
| 2010/0101326 A1* | 4/2010 | Iizuka | G01N 29/12 73/588 |
| 2011/0296923 A1* | 12/2011 | Cataldo | G01N 29/043 73/632 |
| 2012/0255360 A1* | 10/2012 | Tippit, Jr. | G01N 29/221 73/620 |
| 2012/0310551 A1* | 12/2012 | Na | G01N 29/0645 702/39 |
| 2013/0218490 A1* | 8/2013 | Poirier | G01N 29/069 702/56 |
| 2014/0165730 A1* | 6/2014 | Na | G01N 29/0645 73/588 |
| 2015/0039245 A1* | 2/2015 | Langlois | G01N 29/043 702/39 |

* cited by examiner

BO – Beam Overlap
BW – Beam Width
D – Depth

Fig. 3d (prior art)

PO – Probe Overlap
PW – Probe Width

SYSTEM AND A METHOD OF AUTOMATICALLY GENERATING A PHASED ARRAY ULTRASOUND SCAN PLAN FOR NON-DESTRUCTIVE INSPECTION

FIELD OF THE INVENTION

The present disclosure generally relates to a method and a system for conducting non-destructive testing/inspection (later as NDT/NDI), and more particularly to a system and method of automatically generating scan plans for assisting phased array ultrasonic inspections.

BACKGROUND OF THE INVENTION

Phased array ultrasonic testing (PAUT) is an advanced method of ultrasonic testing (UT) that has applications in industrial non-destructive testing (NDT). Common applications are to find flaws in manufactured materials such as welds.

Single-element (non-phased array) probes, known technically as monolithic probes, emit a beam in a fixed direction. To test a large volume of material, a conventional probe must be physically moved or turned to sweep the scan beam through the area of interest.

In contrast, the beam from a PAUT probe can be moved electronically, without moving the probe, and can be swept through a wide volume of material at high speed. The beam is controllable because a PAUT probe is made up of multiple small elements, each of which can be pulsed individually at a computer-calculated timing, forming incidence angles. The term phased refers to the timing, and the term array refers to the multiple elements. The element that contributes to a beam formation is defined as the aperture of the beam; the aperture can include a portion or all of the elements of the PAUT probe.

During typical inspections of welds, multiple ultrasound beams are generated from a single or multiple apertures at various incidence angles. These generate an image showing reflections (or diffractions) of the ultrasonic waves that are associated to defects within the scanned area in the test object. For weld inspection, the interest area, or the scanned area is usually the weld and its surrounding area. For cases where the aperture is fixed and only the angles are changed, the images are called a sectorial scan or S-scan. For cases where the angle is fixed and only the aperture is moved, the images are called a linear scan or E-scan.

In order to have an appropriate coverage of the weld area, it is almost always required to combine inspections from both sides of a weld and it may also be required to do multiple passes on a given side of the weld if a single probe coverage proves insufficient. For defining an inspection plan, standards and normalized practice are the major factors composing the guidelines or codes for defining the probe and beam configurations, an example being Section V of ASME Boiler and Pressure Code—Nondestructive Examination. Such practices are referenced herein as code requirements. For weld inspection, the phased array configuration typically involves the use of a wedge, which defines a first mechanical incidence angle to generate an S-scan with shear waves in the 40 to 70 degree range of the refraction angle. The inspection of a complete weld area also involves a mechanical scan of the weld by moving the probe arrangement parallel to the weld axis.

According to an international code "2010 ASME Boiler & Pressure Vessel Code, 2010 Edition, Section V—Nondestructive Examination" (Herein after as "codes"), the definition of the inspection scan plan associated to weld inspection is as follows. This The scan plan is herein defined as the combination of, a, instrumentation configuration including probe, wedge, and acquisition unit;

b, acoustic setting, including, aperture size and position, focalization setting, beams angle, gating parameters and, c, probe manipulation guideline, including probe to weld distance, maximum inspection speed.

A recurring problem associated to weld inspection using phased array ultrasonic scans is that the combination gets extremely complicated when all the variables, each could have vast range of selections are into play. It is extremely difficult to have an individual trained in such a broad range of expertise as in phased array systems, phased array probes and wedges and in weld structure and flaws.

As can be seen how stiff the challenge is to configure the right scan plan with ranges of parameters for all the factors listed above. A first approach being used in existing practice to address this problem is the use of modeling tools to visualize beams generated by the PAUT probe in the test object. Examples using this approach are "ESBeamTool" from Eclipse Scientific or "SetupBuilder" from Olympus. Whereas this approach to some degrees simplifies certain tasks such as weld coverage and probe placement, it does little to reduce the needs for high-level inspector expertise since a lot of knowledge is still required to bridge the gap between the codes requirement and the instrument selection, configuration and manipulation. More specifically, this approach does not automatically provide templates or models regarding the above listed aspects of a) and b) of a scan plan, and it does not automatically evaluate the above listed aspect c) for probe manipulation either.

Another solution to the problem of defining scan plans is the full integration of all the code requirements in the modeling software as disclosed in US Patent No. US20130218490. Even though this solution has certain success when integrated for the automated inspection of girth weld, when using a dedicated scanner it does have several drawbacks for the PAUT inspection of welds in general. Firstly, a significant amount of codes is needed for PAUT weld inspection in general because each group of codes represents the specific requirements associated to the specific weld usage (piping welds, boiler tubes, pressure vessels, etc.). Secondly, since code interpretation is complicated process and often without a straightforward answer, the code interpretation solely decided by a modeling tool does involve some potential responsibility and acceptance issues.

It would thus be desirable to have a computer aided tool that more easily generates a PAUT scan plan, yet still provides the desired flexibility to allow code requirement interpretation by duly qualified end-users.

SUMMARY OF THE INVENTION

A general object of the present disclosure is to provide a system and method that automatically generate scan plans for assisting phased array ultrasonic inspections based on a set of guidelines and expertise in the groups of instrument configuration, acoustic setting and probe manipulations.

Another object of the present disclosure is to provide an automatic scan generation method for PAUT that first provides a template based on the NDT expertise knowledge in interpreting the codes for a category of inspection tasks. Then the scan generation method further uses a quantitative evaluation method to evaluate specific probe manipulation plan based on the templates and the test object geometry definition.

More specifically, the method of generating a scan plan as presently disclosed involves firstly interpreting the codes with NDT expertise related to aspects of above a) and b) of a scan plan, and generating sets of templates readily available for varies categories of inspection tasks. The templates are stored and made readily available in the phased array system. Then secondly, with a specific inspection task and test object geometry defined, a corresponding template is chosen. Then the presently disclosed method involves employing quantitative evaluation of aspect c) of the above mention scan plan definition, benchmarked by the corresponding template.

Code requirements and PAUT expertise are expressed in quantitative values in the invention, which makes it possible to automatically generate suitable instrument configuration, acoustic setting and probe manipulation guidelines. So, knowledge concerning best practices of PAUT weld inspection can be combined with the various codes that affect these inspections though the use of templates.

DETAILED DESCRIPTION OF THE INVENTION

Figure 1:
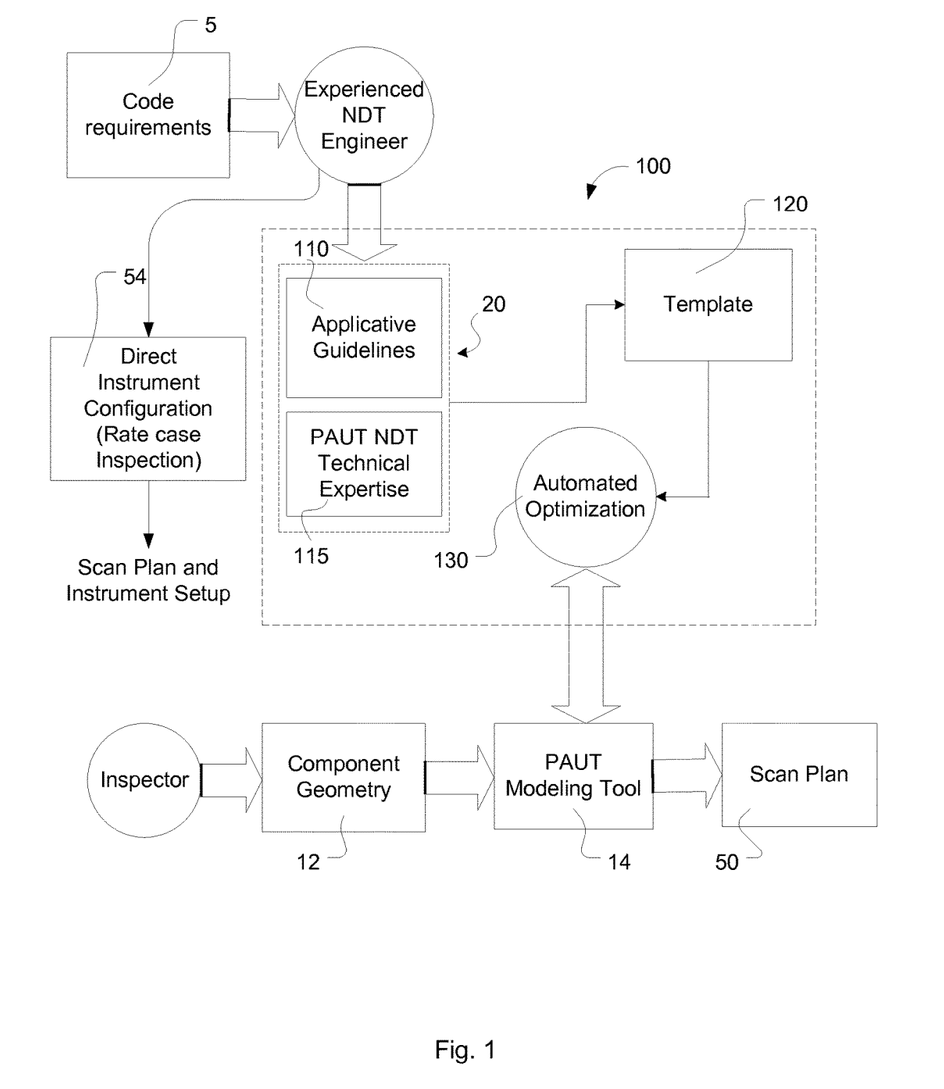
FIG. 1 is a schematic overview the automated scan plan generation process of the present disclosure.

Referring to FIG. 1, the present disclosure, herein referred to as an automatic scan plan generator 100, is comprised of: applicative guidelines 110, a PAUT NDT technical expertise 115, a template 120, and an automated optimization process 130. Applicate guidelines 110 and expertise 115 together form a template generating module 20.

The objective of automatic scan plan generator 100 is to allow an inspector, who might have limited knowledge of PAUT NDT technical expertise 115 and/or code requirements 5, to generate a scan plan 50 and further a suitable instrumentation setup that corresponds to inspecting a test object with component geometry 12 according to code requirements 5. This is achieved by integrating PAUT NDT technical expertise 115 and the decomposition of code requirements 5 into a set of applicative guidelines 110, which encompass the typical aspects covered for the vast majority of inspections. Alternatively, special case inspections that go beyond the scope defined by applicative guidelines 110 can still be addressed through a direct instrument configuration 54 that corresponds to existing practice which necessitates direct involvement of the experienced NDT engineer for the scan plan generation.

Herein all components of the scan plan generator 100 are types of electronic memories and/or processing device, which can be discrete components or part of an integral device.

Automatic scan plan generator 100 makes it possible for template generator module 20 to generate template 120 that integrates the interpretation of code requirements 5 by the NDT engineer through the settings of applicative guidelines 110, PAUT NDT technical expertise 115, and pre-existing default settings that include some of PAUT NDT technical expertise 115 and 'best practices' from applicative guidelines 110. Automated optimization process 130 collaborates with (or is integrated into) a PAUT modeling tool 14 to find a suitable solution for the application of template 120 on component geometry 12 to be specifically inspected.

Figure 2:
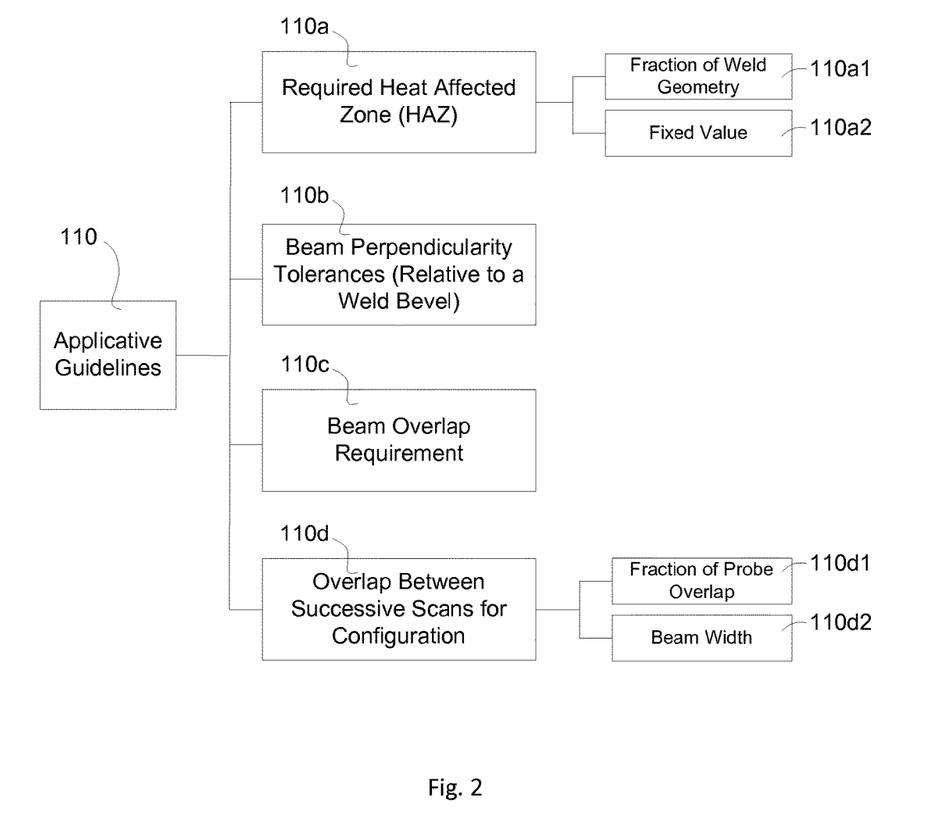
FIG. 2 is a schematic overview of the applicative guidelines that can be applied to the automatically generated scan plan.

Referring to FIG. 2, a novel aspect of automatic scan plan generator 100 is the decomposition of code requirements 5 into applicative guidelines 110 that are specific and quantitative. The preferred embodiment of the present disclosure has applicative guidelines for a weld to be inspected with a pulse echo PAUT: a required Heat Affected Zone (HAZ) applicative guideline 110a, a beam perpendicularity tolerances applicative guideline 110b, a beam overlap requirement applicative guideline 110c, and a probe overlap between successive scans applicative guideline 110d. Other possible embodiments include advanced acquisition methods for ultrasonic information, such as full matrix capture acquisition. It should be noted that other ultrasonic inspection techniques, such as time of flight diffraction (TOFD) and tandem inspection, fall under the scope of the present disclosure.

FIGS. 3a~3d are representations of prior art practices showing exemplary applicative guidelines from code requirement 5. FIGS. 2, 3a~3d together show the process of decomposition of code requirement 5 specifically for weld inspection, which is one of the novel aspects of the present disclosure.

Figures 3A, 3C:
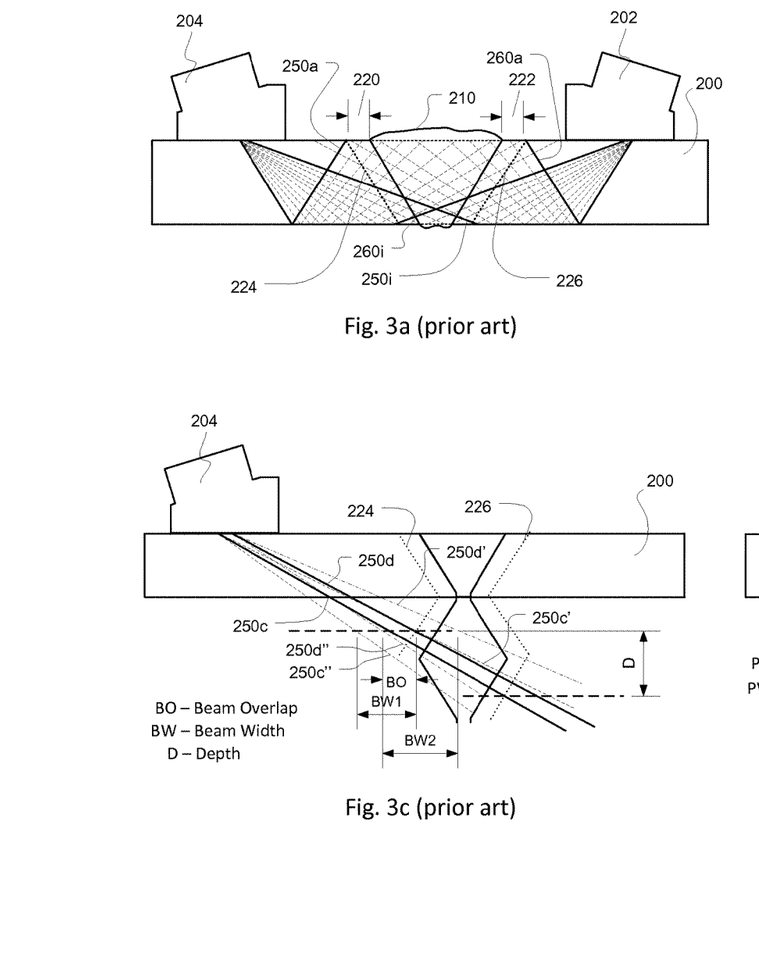
FIG. 3a is a detailed prior art representation of the applicative guideline of a required heat affected zone.
FIG. 3c is a detailed prior art representation of the applicative guideline of beam overlap.

Referring to FIG. 2 and FIG. 3a, required Heat Affected Zone (HAZ) applicative guideline 110a on a test object 200 is illustrated in greater detail, and deals with the size of a HAZ area 220 and a HAZ area 222, in addition to a weld bead 210, that must be inspected by the pulse echo PAUT. Required Heat Affected Zone (HAZ) applicative guideline 110a can be further implemented by a few exemplary subcategory guidelines, such as 110a1 and 110a2 (described below).

The HAZ coverage is managed for a first probe 204 by setting a first beam 250a on a top surface at the limit of HAZ area 220, and by setting a last beam 250i on a bottom surface at the limit of HAZ area 222. For a second probe 202, the same logic applies: use a beam 260a for the top surface at the limit of HAZ area 222, and a beam 260i for the bottom surface of HAZ area 220. The inspection area is thus defined by the full thickness of part thickness, and is defined laterally by the limits of a HAZ coverage 224 and of a HAZ coverage 226.

A subcategory HAZ applicative guideline 110a1 can be used to calculate the HAZ as a corresponding fraction of the weld geometry, such as thickness, top surface, and bottom surface. In the case of using a top surface, HAZ applicative guideline 110a1 can have a recommended value representing size of HAZ area 220 as a fraction of area of the weld bead. In case of length on the top surface of the weld, this is the value of length of 220 on top surface divided by the length of weld bead 210 on top surface. This can apply correspondingly to HAZ weld thickness and HAZ bottom surfaces.

Alternatively, a subcategory HAZ fixed value applicative guideline 110a2 can be defined by the NDT engineer according to the weld being inspected, along with notes and guidelines. In this case, an arbitrary value, instead of a fraction of the size of the test object, is given by the NDT engineer based on the engineer's experience.

Referring to FIGS. 1 and 3a, it is another novel object of the present disclosure, with the size of HAZ coverages 224 and 226 determined by the above process, to automatically set a detection gate in instrument setup that includes only signals originating from the inspection area, such as HAZ coverages 224 and 226. Setting tolerances on the gate position with respect to the inspection area can be performed as an additional applicative guideline (not included in further discussion for simplicity).

Figure 3B:
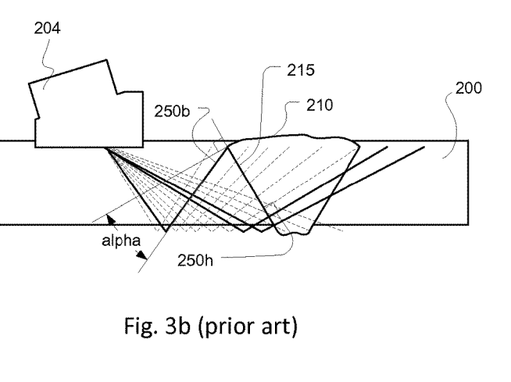
FIG. 3b is a detailed prior art representation of the applicative guideline of tolerances on beam perpendicularity relative to a weld surface.

Referring to FIGS. 2 and 3b, beam perpendicularity tolerances applicative guideline 110b is illustrated in greater detail, which pertains to perpendicularity to weld bevels. A weld bevel 215 is defined here as the surface made on the welded component in preparation to the welding process. Only probe 204 is illustrated on FIG. 3b for clarity, but it will be noted that everything mentioned in further discussion also applies to the probe on the opposite side of the weld and potentially to any supplemental probes that may be required for a given inspection, and falls under the scope of the present disclosure.

Beam perpendicularity tolerances are illustrated as an "alpha" variable. Ideally, all beams should hit a weld bevel with a perpendicular angle such as illustrated for a beam 250h (defined by the component geometry). However this solution is not practical, as it would greatly restrict the coverage of a PAUT probe. Code requirements 5 as a result have been established to allow a given tolerance "alpha" on beam perpendicularity. For a simple bevel configuration, such as the "V" shaped bevel illustrated on FIG. 3b, only a first 250b beam and a last 250h beam hitting the bevel need to be controlled for perpendicularity. Welds involving a curved bevel, such as a "J" shaped bevel, require separate validation for each of the beams.

Referring to FIG. 2 and FIG. 3c, beam overlap (BO) requirement applicative guideline 110c is illustrated in greater detail. Only a beam overlap between a beam 250c and a beam 250d, which is generated by probe 204, is provided for simplicity. (An actual requirement would be to have adequate beam overlap for each successive beam that is generated by the probe over the whole inspection area. For simplicity, multiple reflections are illustrated through mirror images of the bevel on FIG. 3c, which is a common practice in PAUT NDT.)

In order to address the beam overlap requirement, the NDT engineer must first define the beam width BW in function of the depth of the inspected material for each beam. The convention for PAUT NDT is to define the width limits of beam 250c as a position 250c' and a position 250c" and the width limits of beam 250d as a position 250d' and a position 250d" where a defect is to be detected at −6 decibels relative to the same defect at maximum amplitude (i.e. on the centerline of beam 250c). The actual beam width limit can be determined using simulation tools (example: CIVA), mathematic tools, or by using a database of pre-calculated values for each beam to be used for the inspection. Such tools are integrated in automated optimization process 130.

Beam overlap is then defined as the fraction of Beam Overlap/Beam Width (BO/BW), typically expressed as a percentage of beam overlap, where the beam width is the minimum of beam width BW1 and beam width BW2. Beam overlap, or the areas shared by BW1 and BW2, can be defined in a parameter as a required percentage. For a given beam overlap, automatic scan plan generator 100 must define a beam configuration that always meets or exceeds the overlap within a depth range D defined by HAZ coverage 224 and HAZ coverage 226 for each consecutive beam (in this example, beam 250c and beam 250d), which the NDT engineer defines as beam overlap applicative guideline 110c. It is another novel object of the present disclosure to automatically define the number and angular position of each of the beams that define scan plan 50 and instrumentation setup 52, in order to systematically meet or exceed beam overlap requirements set by the NDT engineer over the full inspection area.

Figure 3D:
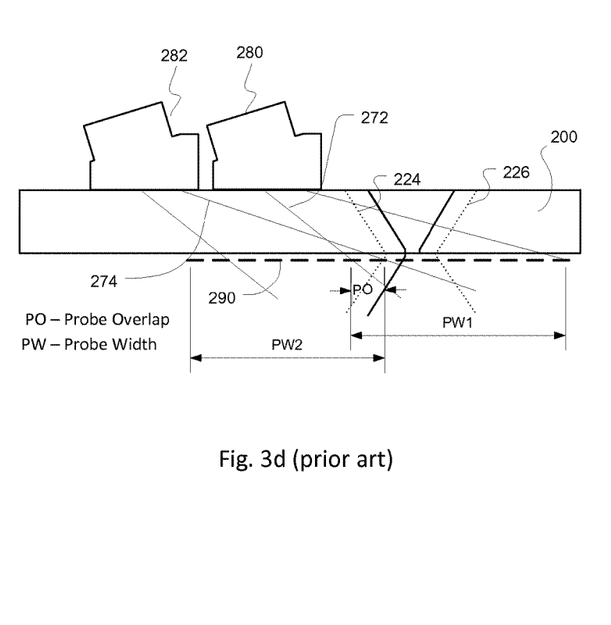
FIG. 3d is a detailed prior art representation of the applicative guideline of overlap between successive scans for configuration.

Referring to FIG. 2 and FIG. 3d, probe overlap between successive scans applicative guideline 110d is illustrated in greater detail, where it is not possible to cover the whole inspection area (including HAZ coverage requirements) from a unique probe position with a given probe. In this case, a probe overlap is evaluated between a last beam 272 corresponding to a probe 280 at a first position closer to the weld and a first beam 274 corresponding to a probe 282 at a second position farther from the weld. Probes 280 and 282 can be the same probe at different positions, or different probes at different position.

A probe overlap PO is measured, at a depth 290 corresponding to the intersection between HAZ coverage 224 and first beam 274, as the horizontal distance between last beam 272 of probe 280 and first beam 274 of probe 282 at this depth. Probe overlap for the purposes of configuration can be further implemented by a few exemplary subcategory guidelines, such as 110d1 and 110d2 (described below).

A probe overlap value as a fraction of the beam width BW can be used, and defined as a parameter by the NDT engineer as a fraction of probe overlap applicative guideline 110d1. In this example, the probe overlap ratio is defined as a fraction of Probe Overlap/Beam Width (PO/BW), where BW is the maximum between the width of beam 274 at depth 290 and the width of beam 272 at depth 290. Alternatively, a fraction of a full probe width PW at depth 290 can also be used as a ratio value of Probe Overlap/Probe Width (PO/PW), where PW is the maximum of a probe width PW1 and a probe width PW2, and defined by the NDT engineer as a beam width applicative guideline 110d2.

FIGS. 2, 3a, 3b, 3c, and 3d encompass most aspects of the code requirements that directly affect the scan plan generation for pulse echo PAUT manual weld inspection, which define the content of applicative guidelines 110 and the interfaces with the NDT engineer. Other applicative guidelines exist for other types of inspections, and fall under the scope of the present disclosure.

Figure 4:
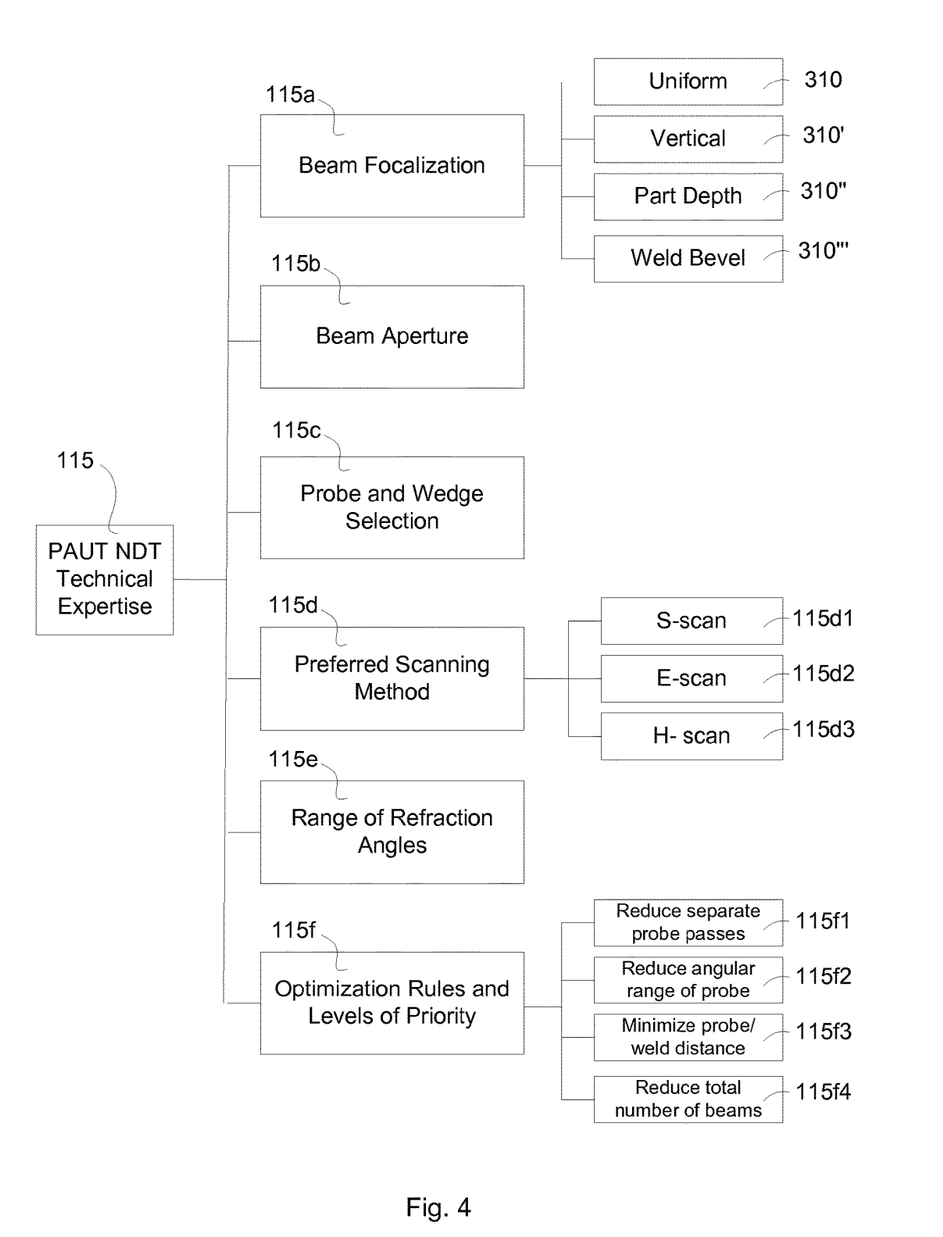
FIG. 4 is a schematic overview of the PAUT NDT expertise that is applied to the automatically generated scan plan.

Referring now to FIGS. 1 and 4, exemplary aspects of PAUT NDT technical expertise 115 that are set by the NDT engineer in template 120 for generating scan plan 50 further include: a beam focalization technical expertise 115a, a beam aperture technical expertise 115b, a probe and wedge selection technical expertise 115c, a preferred scanning method technical expertise 115d, a range of refraction angles technical expertise 115e, and an optimization rules and levels of priority technical expertise 115f.

Referring to FIGS. 4 and 5a-5d, beam focalization technical expertise 115a is the strategy to adapt the focalization from probe 204 to the part geometry. Each beam, such as beam 250c, is to be focalized at a certain position, such as a position 310 in FIG. 5a. It is well known to those skilled in the art that various strategies, or schemes, can be adopted to properly perform a given inspection task. Examples of focalization schemes include a uniform focalization depth to all beams, a focalization on a vertical axis, a focalization after a given through depth distance within the inspected material, and a focalization on the weld bevel. Alternative beam focusing rules can be envisioned by NDT technical expertise, and remain within the scope of the present disclosure.

Figure 5A:
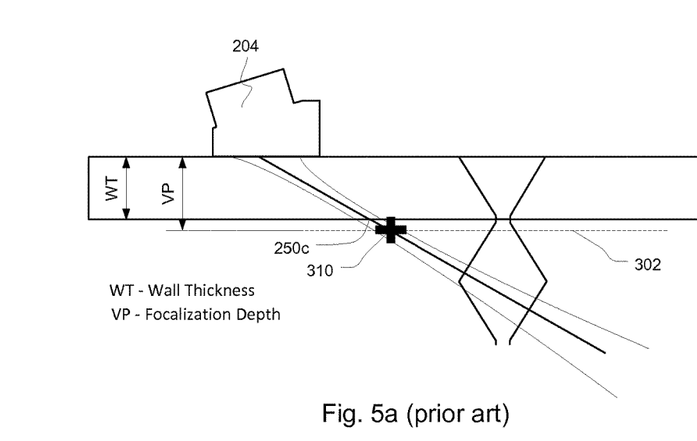
FIG. 5a is a detailed prior art representation of PAUT NDT expertise to provide a uniform focalization depth for all beams traveling in the test object.

Referring to FIGS. 4 and 5a, the preferred embodiment of the invention provides a uniform focalization depth to all beams using a focalization scheme 302, and can be set by the NDT engineer as a fraction of the part wall thickness (WT) according to a focal spot 310. An example of a default parameter is the focalization depth (labeled VP) to be 1.5 times the part wall thickness WT.

Figure 5B:
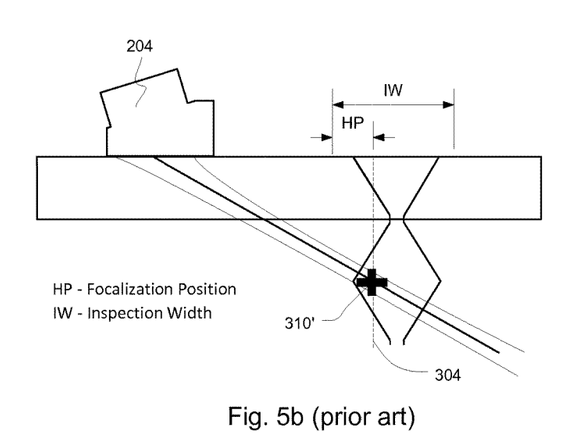
FIG. 5b is a detailed prior art representation of PAUT NDT expertise to provide focalization on a vertical axis.

Referring to FIGS. 4 and 5b, focalization on a vertical axis, according to a focalization scheme 304, can be set by the NDT engineer from a focal spot 310' as a fraction of the total inspected width (IW). An example of a default parameter is the focalization position (labeled HP) be at 0.25 times the inspected width IW.

Figure 5C:
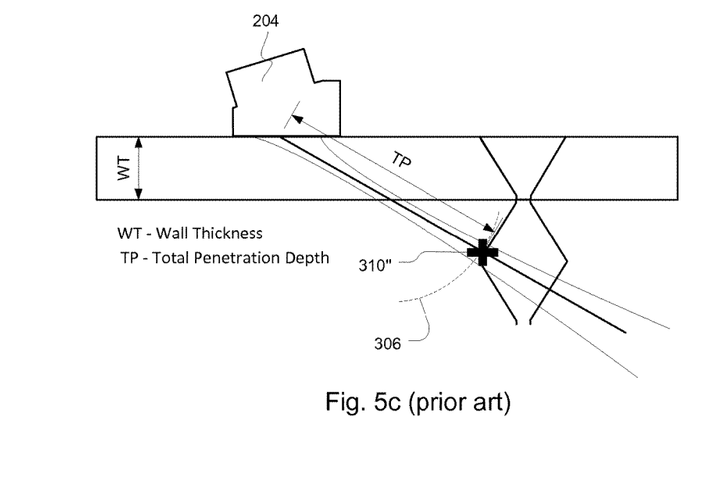
FIG. 5c is a detailed prior art representation of PAUT NDT expertise to provide focalization after a given depth distance within the inspected material.

Referring to FIGS. 4 and 5c, focalization within the inspected material, according to a focalization scheme 306, can be set by the NDT engineer from a focal spot 310" as a fraction of total penetration depth (labeled TP) of the part wall thickness (WT). An example of a default parameter is the focalization of the total material penetration depth TP be at 2 times the part wall thickness WT.

Figure 5D:
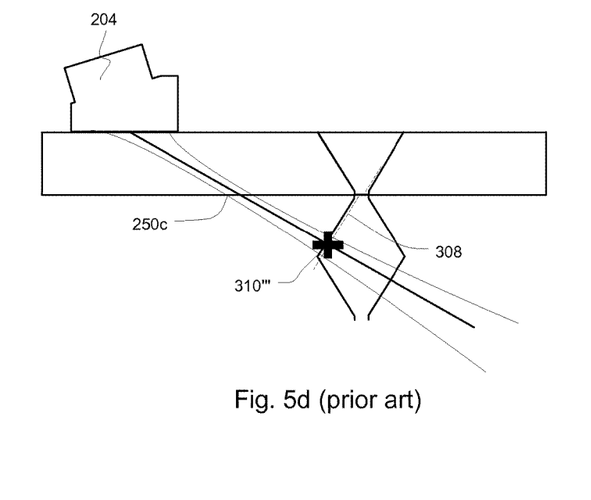
FIG. 5d is a detailed prior art representation of PAUT NDT expertise to provide focalization on a weld bevel.

Referring to FIGS. 4 and 5d, focalization on the weld bevel, according to a focalization scheme 308, can be set by the NDT engineer from the bevel shape directly at focal spot 310''' of a part's upper surface for beams not crossing the bevel.

Referring back to FIG. 4, another exemplary aspect defining the NDT technical expertise is beam aperture technical expertise 115b, which is the number of active elements used to generate a PAUT beam. Beam aperture can be defined as a function of the wall thickness (WT) for specific ranges. Examples include using a beam aperture of 8 up to 0.25 inch WT, then a beam aperture of 16 up to 1 inch WT, and then a beam aperture of 32. Such ranges, including the selection of the number of element and the "up to" WT value, are defined by the NDT engineer.

Yet another exemplary aspect defining the NDT technical expertise is probe and wedge selection technical expertise 115c. Probe and wedge selection is affected by the part's external diameter (OD), the wall thickness WT, and by the weld orientation and geometry relative to the pipe. Typically, separate templates 120 would be correspondingly used for fundamentally different weld geometries by the NDT engineer, as they follow different element of code requirements 5. For example, a first geometry can be a girth weld between two pipes (typically defined in the art as an AOD inspection), a second geometry can be a longitudinal weld along the pipe axis (defined in the art as an COD inspection), a third geometry can be a complex weld at the junction of two pipes (defined in the art as a nozzle, and/or a TKY inspection). For a given template 120, the NDT engineer can maintain a table describing probe and wedge selection as a function of wall thicknesses WT and external diameters OD, along with default values corresponding to the recommended practice for most applications, edited special cases, preferences, and limited probe or wedge availability.

Another aspect defining the NDT technical expertise is preferred scanning method technical expertise 115d. Well known scanning methods include the sectorial scan, or S-scan (defined by a preferred S-scanning method technical expertise 115d1), where the aperture is kept at a fixed position and the refraction angle is swept through a range of angles. Another well-known scanning method is the linear scan, or E-scan (defined by a preferred E-scanning method technical expertise 115d2), where the beam refraction angle is kept fixed and scanning is made by lateral movement of the selected probe aperture.

Figures 5E, 5F:
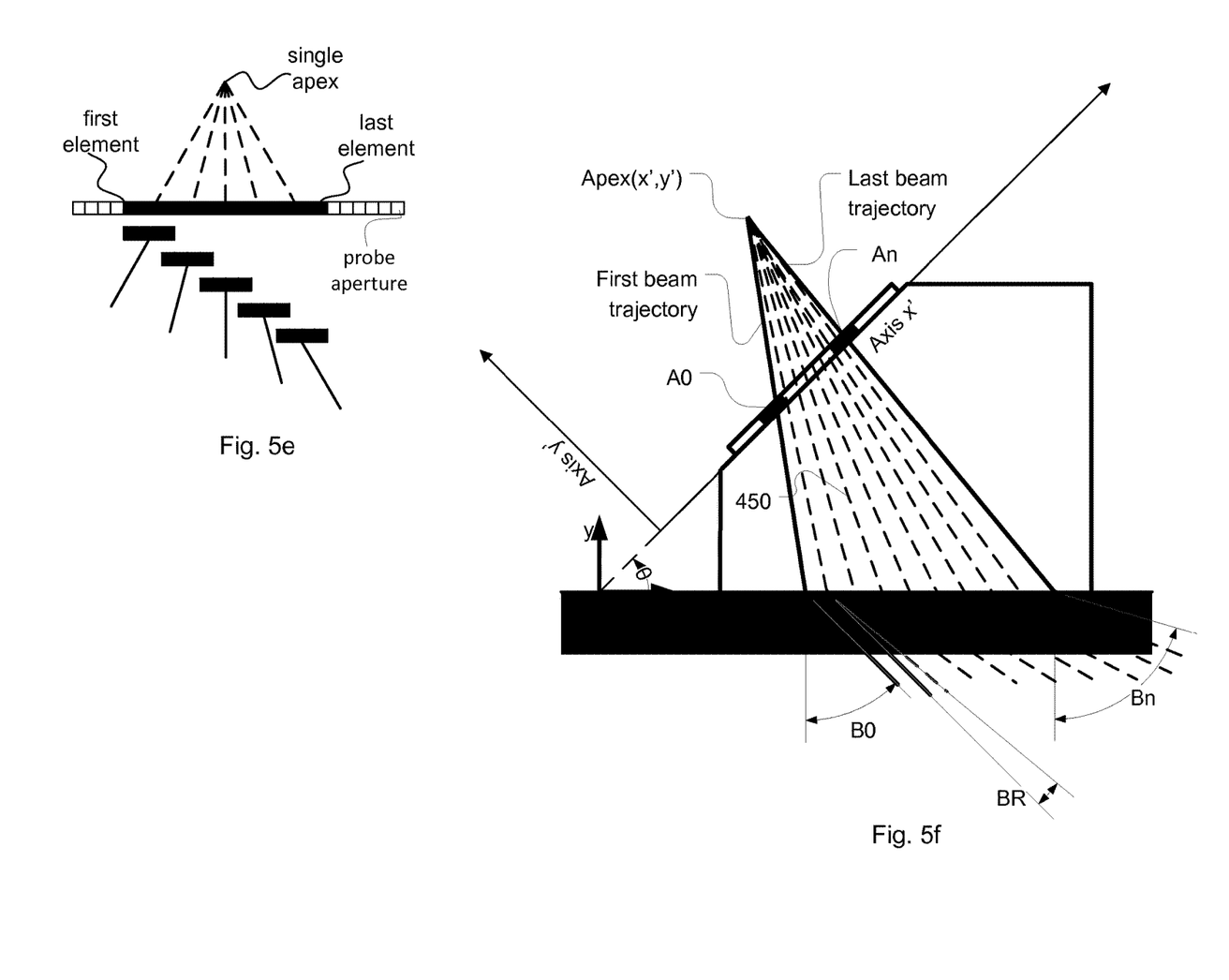
FIG. 5e is a detailed representation of PAUT NDT expertise that illustrates an H-scan.
FIG. 5f is a detailed representation of PAUT NDT expertise that illustrates a multiple scan configuration performed with the configurable parameters of the present disclosure.

Referring to FIGS. 4 and 5e, another novel object of the present disclosure another aspect of technical expertise in choosing scanning method is the usage of an H-scan, which is a hybrid scanning method that combines lateral and angular movement. In this method, the angular sweep is done from a single virtual apex external to the probe, and apertures corresponding to the virtual beam position at the probe/wedge interface are selected to generate the beam. This method increases the probe coverage, and is well adapted to an optimized scan plan, as the additional degrees of liberties offer added value to automated optimization process 130.

Referring to FIGS. 4, 5e, and 5f, an S-scan and E-scan can be considered as a particular case of an H-scan configuration (defined by a preferred H-scanning method technical expertise 115d3). The E-scan is an H-scan with an apex very far (infinite) from the probe and the S-scan is an H-scan with the apex at the probe surface (at the very center of the active aperture). Any scanning definition can be described with the following variables (focalization schemes, beam aperture definition and wedge/probe selection are separate, fixed parameters): first beam angle "B0", last beam angle "Bn", first aperture position "A0", last aperture position "An" and the number of beams "n". From these variables the apex (x',y') position can be automatically calculated and an intermediate beam 450 can be defined. Intermediate beams are rounded to the closest discrete aperture position. The (x',y') reference coordinate is defined here as being aligned with the probe surface and referenced to the probe (i.e. when the probe move so does the x',y' system). For the S-scan, the apex position is set along the (x,o) line. For the E-scan, the apex is set far away on FIG. 5f along an (x,INF) line, where "INF" stands for a very large number.

Returning to FIG. 4, another aspect defining the NDT technical expertise is range of refraction angles technical expertise 115e. This aspect defines the allowed range for the refraction angles knowing that typically low (<40 degrees) and high (>65 degrees) angles are not as reliable as intermediate angles. Since these limits are linked to the probe and wedge selection, the allowed range definition can alternatively be linked to the probe/wedge selection table (or set as range of refraction angles technical expertise 115e).

Yet another aspect defining the NDT technical expertise is optimization rules and levels of priority technical expertise 115f. Levels of priority between optimization rules deal with interferences between these rules. More specifically, for weld inspection with pulse echo PAUT, there are typically four different optimization rules. The first optimization rule, named as technical expertise 115f1, is to reduce the number of separate probe passes that are required to cover an inspection area. The second optimization rule, named as probe technical expertise 115f2, is to reduce the angular range be generated by the PAUT probe. The third optimization rule, named as technical expertise 115f3, is to minimize the distance between the probe and the weld (ideally down to the minimum distance not leading to mechanical interferences, information that should be found in the definition of component geometry 12). The fourth optimization rule, named as technical expertise 115f4, is to reduce the total number of beams that maximizes scan productivity.

One of the novel aspects of the present disclosure is let NDT engineer to assign priority among the optimization rules as described above. More specifically, for the preferred embodiment, the engineer or inspector is asked for a priority score from 0 [not important] to 10 [very important] for each of those optimization rules.

Referring back to FIG. 1, most aspects comprised in applicative guidelines 110 and/or PAUT NDT technical expertise 115 can be transferred from the NDT engineer to the inspector with written notes and guidelines, making it possible to account for special situations where one of the automated template settings is not adapted for a specific situation. It is also possible for the NDT engineer to define which aspect of direct instrument configuration 54 is accessible to the inspector. For example, an inspector can be provided with manual control over a beam aperture along with the following note: "Test 8 and 16 element apertures and use the one that gives you the best signal to noise ratio on the reference defect."

Figure 6:
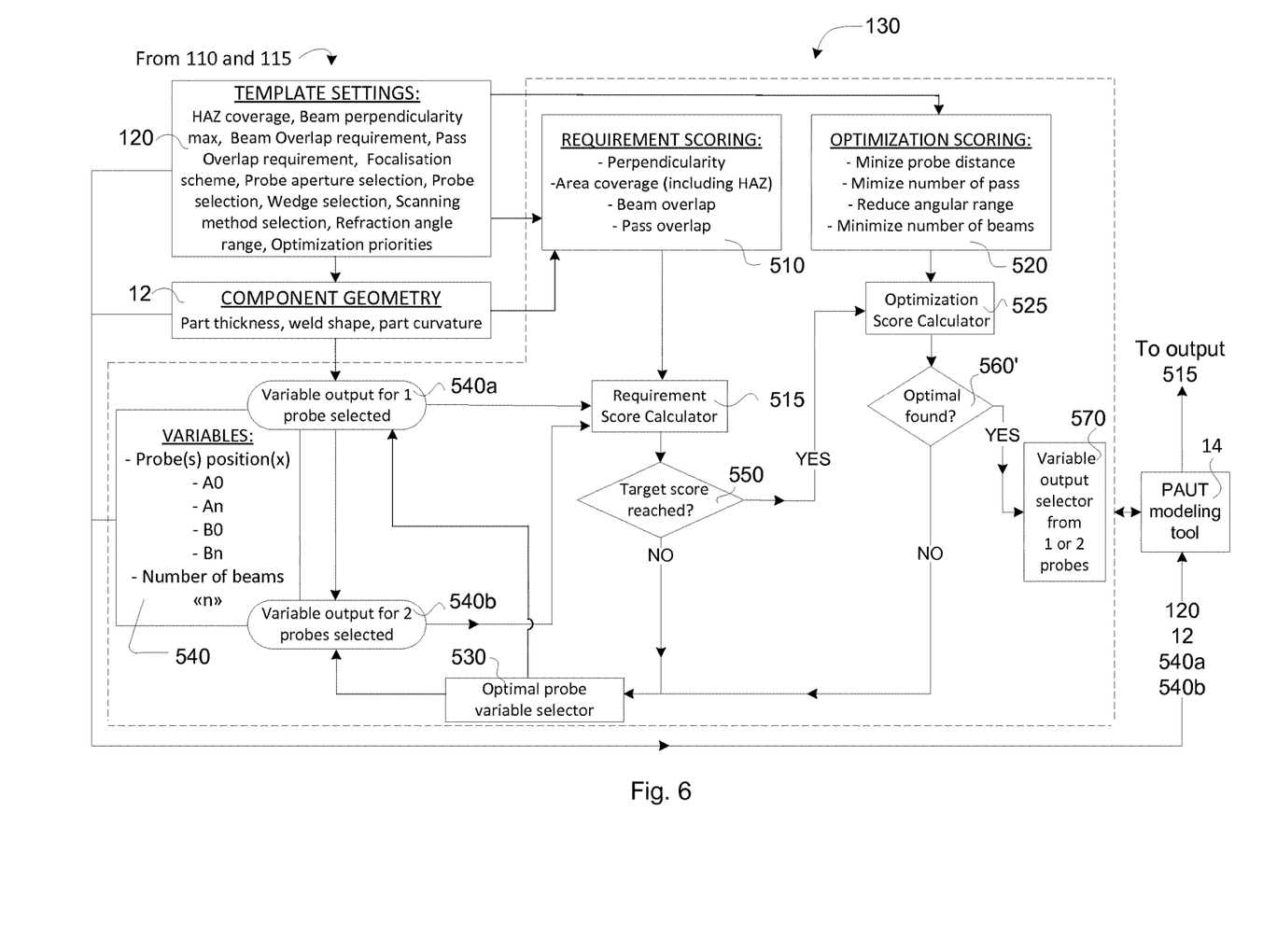
FIG. 6 is a schematic overview of the automated optimization process of the present disclosure.

Referring to FIG. 6, the novelty of generating scan plans as introduced above from applicative guidelines 110 and PAUT NDT technical expertise 115 also further includes an optimization process with scoring mechanism as elaborated in FIG. 6. Each scan plan is comprised of two parts of operation specification. One is the fixed specification represented by template setting module 120 and component geometry module 12. Fixed operation specifications deals with preferences guided by the corresponding applicative guideline 110 and the technical expertise 115 that is not related to specific probe setup and number of runs. The other is the "transient operation specifications" represented by variable input module 540, with two distinct sets of variables: a variable output for one probe setup 540a, and a variable output for two probe setup 540b. For this exemplary case for weld design, the variables of probe setup include those variables above introduced in association with scanning method in FIG. 5f. Probe setup 540a relates to variables of probe setup when one probe is used. Probe setup 540b relates to variables of probe setup when two probes are used.

In FIG. 6, automated optimization process 130 is preferably based on a quantitative scoring system, which comprises two scoring tracks, one called requirement scoring and the other optimization scoring. In the requirement scoring track, the process comprises a requirement scoring guideline 510, a requirement score calculator 515 and a requirement score checker 550. In the optimization scoring track, the process comprises an optimization scoring guideline 520, an optimization score calculator 525. Variable setup module 540 preferably provides probe variable combinations for both 540a and 540b which subsequently feed the variable setup for one-probe and two-probe scenarios to requirement score calculator 515. The input from template setting module 120, component geometry 12, raw variable output for one probe setup 540a, and raw variable output for two probe setup 540b are all provided to the optimization process. A variable output selector 570 selects the better optimized score from either variable output for one-probe setup 540a or variable output for two-probe setup 540b in order to be used with PAUT modeling tool 14

More specifically, requirement scoring module 510 is obtained by evaluating the input from component geometry module 12 with the settings of template 120. Settings of template module 120 are obtained from applicative guidelines 110 based on decomposition of relevant code requirement 5 and NDT expertise 115. Requirement scores on a set of input variables from variable input module 540 are computed against requirements in scoring module 510 and stored in requirement score calculator 515.

Requirement scoring module 510 has guidelines correspond to aspects that must be met in order for template generator module 20 to design and automatically generate scan plan 50. Typically aspects of guidelines included in requirement scoring module 510 are applicative guidelines 110. In the preferred embodiment, the score system is designed to provide a value of 1 for each of the applicative guidelines 110 that are met, and a value of less than 1 for those that are not. For example, perpendicularity relative to the weld bevel can be expressed as (score=1−excessive_perpendicularity/allowed_perpendicularity), area coverage can be expressed as the fraction of the area covered, and beam and pass overlap (BO) can be expressed as the fraction of the target overlap covered (i.e. if BO<BOtarget, then the score is BO/BOtarget; if BO>=BOtarget, then the score is 1). Other scoring systems can also be used as long as the score system provides a fixed target value, and has a gradual slope that makes it possible to improve toward the fixed target value.

When template 120 is applied to component geometry 12, a set of variables from variable output for one probe setup 540a is sent to requirement score calculator 515 in comparison to applicable guidelines requirement scoring guideline 510. Requirement score checker 550 determines if the current variable stored in requirement score calculator 515 meets requirement score scoring guideline 510.

Continuing with the requirement scoring track in FIG. 6, if the set of variables stored in requirement score calculator 515 meets a target score in target score check 550, it is sent to optimization score calculator 525 for further evaluation. If the set of variables does not meet requirement scoring guideline 510, optimal probe variable selector 530 selects another set of variables from variable output for one probe setup 540a and 540b, sends it to requirement score calculator 515 again, wherein the previous set of variables is dynamically stored. The process continues until the set of variables from variable output for one probe setup 540a and 540b in requirement score calculator 515 meets requirement scoring guideline 510. It should be understood that optimization score calculator 525 does not start to work until a requirement score is fully met at requirement score checker 550 or until an optimal is found without meeting target score (in this case there is not solution possible for this probe configuration on the component geometry with the template setting).

Referring to FIGS. 4 and 6, optimization scoring module 520 is based on PAUT NDT technical expertise 115, particularly from optimization rules and levels of priority technical expertise 115f in FIG. 4. Optimization scoring module 520 also uses the input from component geometry module 12 with the settings of template 120. At optimization score calculator 525, specific variable output from 540a and 540b with good requirement scores are calculated against optimization scoring system given in the scoring module 520.

For example, an optimization priority can be set from 0 to 10 by the NDT engineer for defining the priority factor in each of the aspects of PAUT NDT technical expertise 115 that are subject to optimization. The priority factor can then be used as a multiplicative factor over the base score for each of these aspects. Aspects that can gradually change through the optimization are provided a base score that also gradually changes. Base scores must be balanced to accurately reflect the NDT engineer preference, and also to reflect the underlying physics that motivate the optimization rule.

For an exemplary case of weld inspection, in the reduction of the angular range, it is well known to those skilled in the art that the generation of extreme angles, such as a 75 degree shear wave, is not desirable. The optimization scoring system therefore provides a more important scoring benefit to reduce the angular range from 75 to 70 degrees, than from 65 to 60 degrees. Such an optimization receives values in optimization score calculator 525 for the scan plan solution.

Optimal probe variable selector 530 in itself or retrieves from a system memory all the data regarding all previously scored prove variables. The parameters of prove variables and their associated requirement scores and optimization score seeking optimization scores are the basis for selector 530 to conduct a process of mathematical deduction seeking a next optimal set of probe operation parameters. The mathematical deduction process used by selector 530 can use known optimization algorithms such as a gradient descent optimization, a Newton optimization, and an A* search algorithm, to automatically find a next most suitable probe variables, whether it's using one probe or two probes. All variations of implementing the optimization scheme 530 for selecting a more optimal set of probe variables is within the scope of the present disclosure.

After probe variable selector 530 has processed all the variables from 540a and 540b, one of three results can occur. First, if optimal scores have been found for both variable output for one probe setup 540a and variable output for two probe setup 540b, then the outputs are sent to variable output selector 570. Variable output selector 570 selects the variable output with the better optimization score (540a or 540b) to be used with PAUT modeling tool 14. Second, if an optimal score is found for either variable output for one probe setup 540a or variable output for two probe setup 540b, then variable output selector 570 selects the variable output that has the optimal score by default, and uses it with PAUT modeling tool 14. Third, if probe variable selector 530 does not yield variables from variable output for one probe setup 540a or variable output for two probe setup 540b that meet requirement scoring guideline 510, then no suitable scan plan solution can be found for template 120.

It should be noted that the steps of the method herein disclosed can be implemented by using executive software or firmware codes residing in different types of processors not explicitly shown in the present disclosure. Computer memories of varies type are also needed to implement the steps of the herein disclosed method. These processors and memory can be part of already existing PAUT system, modified with the spirit of the present disclosure, or it can be newly designed processors and memories implementing the steps of herein disclosed method. However the usage of such industrially readily available processors and memories are all within the scope of the present disclosure.

It should further be noted that the steps of the methods herein disclosed can also be implemented in form of executable software that is independent of any particular phased array apparatus. The software can reside in any stand-alone electronic media and ready to be imported to any phased array apparatus. Such variation is also within the scope of the present disclosure.

It yet should further be noted that the steps of the methods or the functional modules carrying out the method as herein disclosed can be combined together or spitted into separate sub-steps or units in any fashion, all of which are within the scope of the present disclosure.

The present disclosure is not limited to the use of a weld inspection, which is herein used as an exemplary embodiment. Other types of probes and test objects may be suited for using the method and apparatus as disclosed.

What is claimed is:

1. A method of preparing and using a scan plan for a phased array ultrasonic testing (PAUT) inspection system, the system configured to be coupled with a plurality of probes for conducting a plurality of categories of inspection tasks on a plurality of corresponding test objects, the inspection tasks need to be done in accordance to a set of standardized codes and a set of expertise rules given according to PAUT expertise and operated by a field inspector, the scan plan including instrument setup, acoustic setup, and positioning and movement of the plurality of probes, the method comprising the steps of:
defining a set of standardized codes and expertise rules templates, each for a category of said plurality of categories of inspection tasks, by decomposing the codes, forming applicative guidelines and integrating the expertise rules for the plurality of categories of inspection tasks, defining a selected inspection task out of the plurality of categories of inspection tasks with a selected one of said plurality of test objects, and defining the category of the selected inspection task and accordingly selecting a corresponding one of said set of templates;

defining a set of requirement scoring schemes, each including a target requirement score and an optimization scoring scheme according to the selected corresponding template, defining geometric definitions of the selected test object, as part of the scan plan, determining at least one selected probe out of the plurality of probes, and N sets of probe operation parameters for the at least one selected probe, one at a time, using one of the N sets of probe operation parameters and the geometric definitions to seek requirement scores using the requirement scoring schemes and selecting m sets of probe operation parameters that reached the target requirement score, wherein m is less than or equal to N, one at a time, seeking optimization scores by using the optimization scoring schemes among the m sets of operation parameters and finding a set of probe operation parameters to be the optimal set of probe operation parameters, and using the scan plan with the selected corresponding template and the optimal set of probe operation parameters to conduct the selected inspection task inspecting the selected test object.

2. The method of claim 1, wherein the step of defining a set of standardized codes and expertise rules templates is configured to be conducted prior to and being independent of the selected inspection task, and wherein the templates are stored in a memory of the instrument.

3. The method of claim 1, wherein the instrument setup includes the determination of the at least one selected probe, corresponding wedges and an acoustic unit for the selected task.

4. The method of claim 3, wherein the acoustic setup includes setting aperture size, aperture position, focalization setting, beam angles and gating parameters for the at least one selected probe and the acoustic unit.

5. The method of claim 4, wherein each set of the N sets of probe operation parameters includes positions, scan trajectory and the number of at least one probe relative to the selected test object, number of apertures, number of phased array beams and corresponding beam angles for the at least one selected probe.

6. The method of claim 5, wherein the probe operation parameters of the at least one selected probe include a corresponding set of probe operation parameters for a one-probe setup and/or a two-probe setup for the selected task.

7. The method of claim 5 further including a step of selecting a probe setup achieving a highest optimization score among the usage of the one-probe setup or the two-probe setup.

8. The method of claim 5, wherein the test object is a weld along a weld line, wherein the weld includes a heat affected zone, at least two weld bevels, a weld top-surface width and a weld bottom width.

9. The method of claim 8, wherein the requirement scoring scheme includes a predetermined requirement of covering the heat affected zone, having phase array beams to be perpendicular to the weld bevels and a predetermined requirement for overlap between two successive beams of the at least one selected probe.

10. The method of claim 8, wherein the requirement scoring scheme includes a predetermined requirement of maintaining a predetermined overlap distance between a first beam of a first probe of the at least one selected probe and the last beam of a second probe of the at least one selected probe.

11. The method of claim 10, wherein the requirement scoring scheme includes a predetermined requirement of maintaining a predetermined fraction of the overlap distance and a beam width, wherein the beam width is the maximum between the width of the first beam and the last beam at a predetermined depth.

12. The method of claim 10, wherein the first probe has a first probe width and the second probe has a second probe width, and the requirement scoring scheme includes a predetermined requirement of maintaining a predetermined fraction of the overlap distance and a probe width, wherein the probe width is the maximum of the first probe width and the second probe width.

13. The method of claim 8, wherein the requirement scoring scheme includes a set of expertise rules related to any of the following: beam focalization, beam aperture, probe and wedge selection, scanning method and range of refraction angles.

14. The method of claim 8, wherein the optimization scoring scheme is determined by a set of optimization rules including at least one of the following: a first optimization rule to reduce a number of separate probe passes that are required to cover the selected inspection task, a second optimization rule to reduce an angular range generated by the at least one selected probe, a third optimization rule to minimize a distance between the at least one selected probe and the weld according to the geometry and a fourth optimization rule to reduce a total number of beams.

15. The method of claim 1, wherein the requirement scoring scheme scores in such a way that closer the conditions set by the probe operation parameters to that of the corresponding template, higher the requirement score is.

16. The method of claim 1, wherein the step of seeking optimization scores includes using a step of mathematically deducing a next optimal set of probe operation parameters based on all available set of probe operation parameters and their corresponding requirement scores and optimization scores.

17. A phased array ultrasonic testing (PAUT) inspection apparatus configured for conducting a plurality of inspection tasks on a plurality of corresponding test objects with the usage of a plurality of probes according to standardized codes and a set of rules of industrial expertise given according to PAUT expertise and operated by a field inspector, wherein each of the plurality of inspection tasks is performed according to a scan plan including instrument setup, acoustic setup, and positioning and movement of the plurality of probes, the instrument comprising:
a template module configured to form a set of the standardized codes and the rules of industrial expertise templates, each for a category of the plurality of inspection tasks, by decomposing the standardized codes, forming applicative guidelines and integrating the rules of industrial expertise for the categories of the plurality of inspection tasks,
an electronic memory storing the templates,
a test object geometry module and a PAUT modeling tool configured to define a selected inspection task out of the plurality of inspection tasks with a selected test object, to define the category of the selected task and accordingly select a corresponding one of said templates, which yields at least one selected probe out of the plurality of probes,
an automated optimization engine defining a set of requirement scoring scheme, each including a target requirement score and an optimization scoring scheme finding the most optimal optimization scores according to the selected corresponding template,
wherein the optimization engine further evaluates N sets of probe operation parameters for the at least one selected probe, one at a time, using one of the N sets of probe operation parameters to seek requirement scores using the requirement scoring schemes,
and with m set of probe operation parameters achieving the target score, wherein m is less than or equal to N, the optimization engine further configured to seek optimization scores using the optimization scoring schemes for the m set of probe operation parameters and to find a set of probe operation parameters to be the optimal set of probe operation parameters, and,
the PAUT modeling tool uses the corresponding template and the optimal set of probe operation parameters to generate the scan plan for the selected task, and uses the scan plan to conduct the selected inspection task inspecting the selected test object.

18. The apparatus of claim 17, wherein the template module is configured to be independent of the selected inspection task.

19. The apparatus of claim 17, wherein the instrument setup includes yielding the at least one selected probe, corresponding wedges and an acoustic unit for the selected inspection task.

20. The apparatus of claim 19, wherein the acoustic setup includes aperture size, aperture position setting, focalization setting, beam angles and gating parameters for the at least one selected probe and the acoustic unit.

21. The apparatus of claim 19, wherein each set of the N sets of probe operation parameters includes positions, scan trajectory and the number of at least one probe relative to the selected test object, number of apertures and number of phased array beams and corresponding beam angles for the at least one selected probe.

22. The apparatus of claim 19, wherein the probe operation parameters of the at least one selected probe include a corresponding set of probe operation parameters for a one-probe setup and/or a two-probe setup for the selected inspection task.

23. The apparatus of claim 22, wherein the test object is a weld along a weld line, wherein the weld includes a heat affected zone, at least two weld bevels, a weld top-surface width and a weld bottom width, and,
wherein the requirement scoring scheme includes a predetermined requirement of covering the heat affected zone, having phase array beams to be perpendicular to the weld bevels and a predetermined requirement for overlap between two successive beams of the at least one selected probe.

24. The apparatus of claim 23, wherein the requirement scoring scheme further includes a set of rules of industrial expertise related to any of the following: beam focalization, beam aperture, probe and wedge selection, scanning method and range of refraction angles.

25. The apparatus of claim 24, wherein the optimization scoring scheme is determined by a set of optimization rules including at least one of the following: a first optimization rule to reduce a number of separate probe passes that are required to cover the selected inspection task, a second optimization rule to reduce an angular range generated by the at least one selected probe, a third optimization rule to minimize a distance between the at least one selected probe and the weld according to the geometry and a fourth optimization rule to reduce a total number of beams.

* * * * *